(12) United States Patent
Murata

(10) Patent No.: US 6,306,915 B1
(45) Date of Patent: Oct. 23, 2001

(54) METHODS OF MAKING AN EMULSIFIED COMPOSITION

(75) Inventor: Katsumi Murata, Tokyo (JP)

(73) Assignee: Kibun Food Chemifa Co., Ltd, Tokyo (JP)

( * ) Notice: Subject to any disclaimer, the term of this patent is extended or adjusted under 35 U.S.C. 154(b) by 0 days.

(21) Appl. No.: 09/370,211

(22) Filed: Aug. 9, 1999

(30) Foreign Application Priority Data

Aug. 7, 1998 (JP) .................................................. 10-224048

(51) Int. Cl.$^7$ .............................. B01F 3/08; B01F 17/56; C07H 15/00; A61K 31/70
(52) U.S. Cl. ........................ 516/67; 516/926; 516/925; 514/25; 514/938; 514/939; 536/17.9
(58) Field of Search .................. 516/67, 75, 925, 516/926; 424/401; 536/17.9; 514/25, 938, 939

(56) References Cited

U.S. PATENT DOCUMENTS

| | | | |
|---|---|---|---|
| 5,152,928 | * 10/1992 | Kudo et al. .......................... | 516/13 |
| 5,362,418 | * 11/1994 | Yamasaki et al. .................. | 514/939 |
| 5,672,693 | * 9/1997 | Kawahara ........................... | 536/17.9 |
| 5,679,357 | * 10/1997 | Dubrief et al. .................... | 424/401 |
| 5,700,456 | * 12/1997 | Dubrief et al. .................... | 424/401 |
| 5,780,441 | * 7/1998 | Higa et al. ......................... | 514/25 |
| 5,849,716 | * 12/1998 | Akimoto et al. ................... | 514/25 |

FOREIGN PATENT DOCUMENTS

| | | |
|---|---|---|
| 4207893 | 1/1994 | (AU) . |
| 2239295 | * 11/1998 | (CA) . |
| 61-286307 | 12/1986 | (JP) . |
| 1-242690 | 9/1989 | (JP) . |
| 2-48520 | 2/1990 | (JP) . |
| 4-159203 | 6/1992 | (JP) . |
| 5-39485 | 2/1993 | (JP) . |
| 6-157283 | 6/1994 | (JP) . |
| 6-80007 | 10/1994 | (JP) . |
| 7-133217 | 5/1995 | (JP) . |
| 7285827 | 10/1995 | (JP) . |
| 9-301820 | * 11/1997 | (JP) . |

OTHER PUBLICATIONS

DWPI on West, week 199806, London: Derwent Publications, Ltd., AN 1998–059047, , JP 09301820 A (Pola Chem Ind Inc) abstract, 1998.*

Hirai et al., "Characteristics and applications of fine o/w emulsions prepared by D–Phase Emulsification" *Fragrance Journal*, pp. 34–41, (1993), (Month Unknown).

* cited by examiner

Primary Examiner—Daniel S. Metzhaier
(74) Attorney, Agent, or Firm—Browdy and Neimark

(57) ABSTRACT

The present invention provides a method of making an emulsified composition employing an emulsifier containing a sphingoglycolipid which has a structure represented by the following formula:

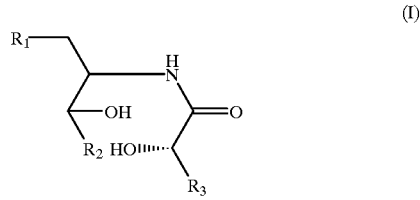

(I)

wherein $R_1$ is a saccharide moiety which consists of three to four hexoses selected from the group consisting of uronic acid, glucosamine, galactose, and mannose, or one uronic acid; $R_2$ is an alkyl group, which may have a cycloalkyl group, an alkenyl group, or an alkynyl group; and $R_3$ is an alkyl group. The alkyl group, the alkenyl group and the alkynyl group may have a normal chain or a branched chain, and may be substituted or unsubstituted. The emulsifier of the present invention has marked moisturizing effect, skin roughening preventing effect, and emulsifying effect.

10 Claims, No Drawings

METHODS OF MAKING AN EMULSIFIED COMPOSITION

BACKGROUND OF THE INVENTION

1. Technical Field

The present invention relates to an emulsifier containing a sphingoglycolipid having a specific structure. Because the emulsifier of the present invention has excellent moisturizing effect, skin roughening preventing effect, and emulsifying effect, it can widely be used for cosmetic and medical products. Moreover, the present invention also relates to a method for producing an emulsified composition using the emulsifier, and an emulsified composition using the emulsifier.

2. Description of Related Art

Skin roughening is caused by loss of too much moisture from skin surface, when air is dry, skin is washed or the like. Further, since various chemicals have overflowed in the society in these days, the functions of the skin having touched these chemicals are likely to be deteriorated, and thus the skin roughening state is often caused by decrease of the lipid secretion function or the like. For this reason, it has been desired to provide a composition that can prevent skin roughening in advance and has excellent moisturizing effect.

As active compounds having moisturizing effect, various compounds, mainly water-soluble polyhydric alcohols, have been provided so far. Among those, some are already put into practical use like propylene glycol. However, many of those moisturizing compounds put into practical use are accompanied by unpleasant feeling when they are applied to the skin, or exhibit only insufficient moisturizing effect. Therefore, it is still desired to develop a novel moisturizing compound.

Under such a situation, sphingoglycolipids attract attentions as a safe moisturizing compound.

For example, it is disclosed that sphingoglycolipids have skin moisture retaining effect in Japanese Patent Unexamined Publication (KOKAI) Nos. 1-242690, 2-48520, 4-159203, and Japanese Patent Publication (KOKOKU) No. 6-80007. However, structures or compositions of sphingoglycolipids that are used in the examples of these patent documents are not clarified.

Moreover, Japanese Patent Unexamined Publication (KOKAI) No. 6-157283 discloses a moisturizing cosmetic for skin external application which is characterized by inclusion of a sphingoglycolipid represented by a specific general formula as one of its ingredients. However, the saccharide portion mentioned in the general formula is described simply as a saccharide residue, and it does not refer to the detail of the saccharide portion.

Thus, while it has been known that sphingoglycolipids have moisturizing effect, substantially no research has been made about the chemical structures of the sphingoglycolipids having such moisturizing effect.

As a document that specifically mentions sphingoglycolipids having the moisturizing effect, Japanese Patent Unexamined Publication (KOKAI) No. 61-286307 can be mentioned. This patent document describes that gangliosides have skin moisturizing effect and skin softening effect, and discloses a skin cosmetic containing a ganglioside or a salt thereof. Gangliosides are sphingoglycolipids characterized by inclusion of an aminosaccharide and sialic acid in addition to a neutral saccharide.

Further, Japanese Patent Unexamined Publication (KOKAI) Nos. 5-39485, 7-133217, and 7-285827 disclose agents for skin external application which utilize cerebrosides. Cerebrosides are sphingoglycolipids consisting of fatty acid, sphingosine base, and neutral saccharide (galactose or glucose) in a molar ratio of 1:1:1.

As described above, as for the sphingoglycolipids having the moisturizing effect to the skin, only several kinds of structures have been specified. Therefore, it has not been elucidated at all for what kind of structure of sphingoglycolipids generally impart potential moisturizing effect to them. For this reason, even when a mixture of sphingoglycolipids was obtained from a living organism, the mixture must be used as it was since such a potential active ingredient was unknown, and thus the moisturizing effect could not be properly enhanced by purification. Moreover, because any general structure of sphingoglycolipids having potential activity has not been elucidated, moisturizers have also scarcely been produced by chemical synthesis.

Further, to use as an ingredient of cosmetics and the like, an ingredient must have a property that it can be easily formulated as cosmetics in addition to the moisturizing effect and skin roughening preventing effect. Since many of cosmetics are composed of an emulsified composition of oil component and aqueous component, ease of utilization for an emulsified composition is very important for the ingredient. Therefore, if an active ingredient which also exhibit emulsifying effect in addition to the moisturizing effect or the skin roughening preventing effect can be provided, it will be very useful. However, sphingoglycolipids have never been studied from such a viewpoint so far.

In view of these problems of the prior art, the present inventors conducted studies aiming at identifying structures of sphingoglycolipids having potential moisturizing effect, skin roughening preventing effect, and emulsifying effect. That is, the object of the present invention was to identify a group of sphingoglycolipids having potential moisturizing effect, skin roughening preventing effect, and emulsifying effect, and thereby provide an emulsifier containing them. Further, the present invention also aimed at providing an emulsified composition using such an emulsifier, and an effective method for producing an emulsified composition using such an emulsifier.

SUMMARY OF THE INVENTION

In order to achieve the aforementioned objects, the present inventors diligently conducted studies. As a result, they found that sphingoglycolipids of a specific structure have excellent moisturizing effect, skin roughening preventing effect, and emulsifying effect, and thus accomplished the present invention.

That is, the present invention provides an emulsifier characterized in that it contains a sphingoglycolipid having a structure represented by the following formula.

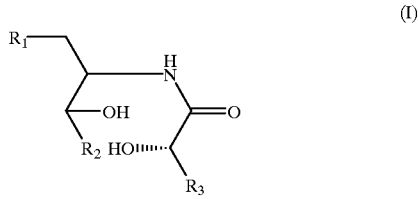

In the above formula, $R_1$ is a saccharide moiety which consists of three to four hexoses selected from the group consisting of uronic acid, glucosamine, galactose, and mannose, or one uronic acid. As for the three to four hexoses, their number, linking order, linking scheme, and optical isomerism are not particularly limited so long as they are consist of a combination of one to four saccharides selected from uronic acid, glucosamine, galactose, and mannose. Examples of the combination constituting $R_1$ include, for example, those consisting of only one uronic acid, those consisting of four hexoses of uronic acid, glucosamine, galactose, and mannose, those consisting of three hexoses of uronic acid, glucosamine, and galactose, and those consisting of four hexoses of uronic acid, galactose, and two glucoses.

As specific examples of $R_1$, the following Structures A to D can be exemplified.

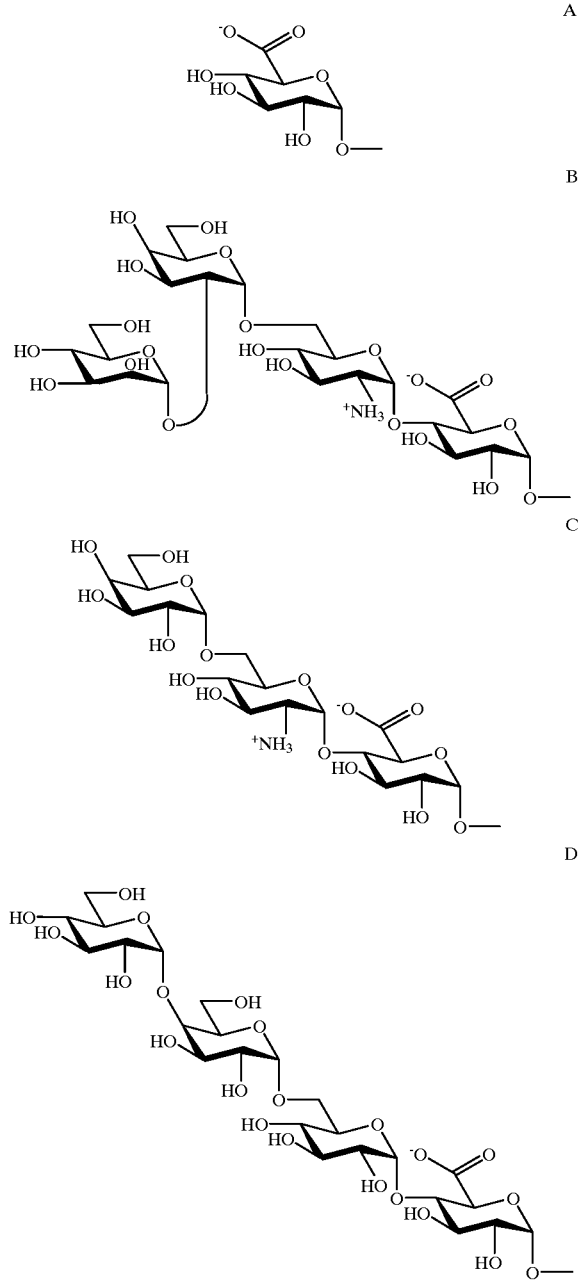

In the formula (I), $R_2$ is an alkyl group, which may have a cycloalkyl group, an alkenyl group, or an alkynyl group. While the carbon number of $R_2$ is not particularly limited, it is preferably within the range of 15–25. The alkyl group, the alkenyl group and the alkynyl group for $R_2$ may have a normal chain or a branched chain, and they may be substituted with a hydroxyl group and the like, or may not have any substitutent. In particular, the alkyl group may contain a cycloalkyl group such as cyclopropyl group in its chain. Location of the double bond of the alkenyl group and location of the triple bond of the alkynyl group are not particularly limited.

As specific examples of $R_2$, the following Structures a to c can be exemplified.

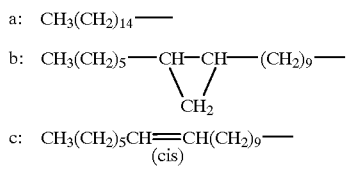

In the formula (I), $R_3$ is an alkyl group. The alkyl group for $R_3$ may have a normal chain or a branched chain, and they may be substituted with a hydroxyl group and the like, or may not have any substitutent. The carbon number of the alkyl group is usually within the range of 1–50, preferably within the range of 15–25. As specific examples of $R_3$, a normal chain alkyl group having a carbon number of 12 can be exemplified.

As a group of the sphingoglycolipids preferably used for the emulsifier of the present invention, sphingoglycolipids of the formula (I) wherein $R_1$ is a saccharide moiety represented by Structure A, B, C, or D, and $R_3$ is a normal chain alkyl group having a carbon number of 12 can be mentioned.

Further, as another preferred group of the sphingoglycolipids, sphingoglycolipids of the formula (I) wherein $R_2$ is represented by Structure a, b, or c, and $R_3$ is a normal chain alkyl group having a carbon number of 12 can be mentioned.

As a particularly preferred group of the sphingoglycolipids, sphingoglycolipids of the formula (I) wherein $R_1$ is a saccharide moiety represented by Structure A, B, C, or D, $R_2$ is represented by Structure a, b, or c, and $R_3$ is a normal chain alkyl group having a carbon number of 12 can be mentioned.

The emulsifier of the present invention may contain one or more kinds of these sphingoglycolipids represented by the formula (I). When two or more kinds of sphingoglycolipids are contained in combination, ratio of the sphingoglycolipids is not particularly limited.

The sphingoglycolipids represented by the formula (I) can be obtained by extraction from cells containing the sphingoglycolipids. Since the sphingoglycolipid is contained in cells of bacteria belonging to the genus Sphingomonas, the sphingoglycolipids represented by the formula (I) can be obtained by extraction using any one of bacteria belonging to the genus Sphingomonas. Because the sphingoglycolipids represented by the formula (I) are insoluble in acetone, the cells are preferably washed with acetone before the extraction. A solvent used for the extraction of the sphingoglycolipids of the formula (I) is preferably an alcoholic solvent such as methanol, or a mixed solvent of an alcoholic solvent and a polar solvent such as chloroform, from the viewpoint of yield. However, any solvent other than these may also be used so long as it is a solvent solubilizing the sphingoglycolipids.

When a mixture of sphingoglycolipids is obtained, each component can be separated according to a well known method in the art. For example, sphingoglycolipids having each of Structure A, Structure B, Structure C, and Structure D as $R_1$ can be completely separated by chromatography. When a chloroform/methanol mixed solution is used as an eluate, each sphingoglycolipid is eluted in the order of those having Structure A, Structure C, Structure D, and Structure B. Therefore, they can be very easily separated. Separation conditions of chromatography, such as chromatography material, eluate, elution speed, pressure, and temperature, can suitably be controlled. Further, the separation can also be achieved by allowing an reagent which selectively react with a specific substance contained in a mixture of sphinglycolipids to act on the mixture to produce a derivative of the substance, and separating the derivative utilizing its chemical or physical property.

When *Sphingomonas paucimobilis* is used as the bacterium, sphingoglycolipids having Structure A and sphingoglycolipids having Structure B as $R_1$ in the formula (I) are generally obtained. When *Sphingomonas capsulate* is used, sphingoglycolipids having Structure A and sphingoglycolipids having Structure C as $R_1$ in the formula (I) are generally obtained. Further, when *Sphingomonas adhaesiva* is used, sphingoglycolipids having Structure A and sphingoglycolipids having Structure D as $R_1$ in the formula (I) are generally obtained. Therefore, a desired sphingoglycolipid can be efficiently obtained by selecting bacterium based on such information.

The sphingoglycolipids represented by the formula (I) can also be synthesized by combination of well known synthetic processes. For example, the saccharide and the sphingosine moieties are synthesized beforehand, or extracted from cells, and each of the sphingoglycolipids represented by the formula (I) can be prepared by forming an amide bond between the moieties.

The form of the emulsifiers containing the sphingoglycolipids represented by the formula (I) is not particularly limited. Therefore, they can take any form such as solid, liquid, paste, jelly, and powder. In order to form such forms, for example, the emulsifiers can be solidified by using a gelling agent, or made into dispersion by using a liquid. It can also be made into a solution by adding a solvent, or made into powder by spray drying.

It was confirmed that the emulsifier of the present invention had excellent moisturizing effect and excellent skin roughening preventing effect, gave proper moisture to the skin surface, and maintained smoothness of the skin. That is, the emulsifier of the present invention can retain moisture of the skin over a long period of time. Such an effect of the present invention is considerably superior to those of gangliosides and galactocerebrosides, which are the sphingoglycolipids of which moisturizing property has been confirmed. Therefore, the emulsifier of the present invention can be used very effectively, when improvement of skin roughening, improvement of keratin, or protection of skin is required.

Moreover, the emulsifier of the present invention also has anti-atopy effect. Therefore, the emulsifier of the present invention is also applicable to prevention and medical treatment of atopic dermatitis.

Furthermore, the emulsifier of the present invention is characterized by its high emulsifying effect. Therefore, by using the emulsifier of the present invention, an emulsified composition can be produced without further using other commonly used emulsifiers. Therefore, when the emulsifier of the present invention is used, an emulsified composition simultaneously exhibiting the moisturizing effect, skin roughening preventing effect, and emulsifying effect can be obtained, and thus it is very convenient. That is, in the conventional production of an emulsified composition utilizing a moisturizing component and skin roughening preventing component, an emulsifier must be added separate from those components. However, such a situation can be avoided by using the emulsifier of the present invention. Therefore, if the emulsifier of the present invention is utilized, the number of active ingredients can be reduced, and thus production cost can be reduced.

The emulsifier of the present invention can be used for, for example, production of cosmetics or medical products. For example, it can be used for the production of toilet soap, shampoo, face washer, hair rinse, eye cream, eye shadow, cream and milky lotion, toilet water, perfume, makeup powder, cosmetic oil, hair cosmetic, hair dye, cream perfume, powder, pack, shaving cream, shaving lotion, suntan oil, sunscreen oil, suntan lotion, sunscreen lotion, suntan cream, sunscreen cream, foundation, powder perfume, rouge, mascara, eyebrow shadow, nail cream, manicure, manicure remover, hair washer, bath cosmetic, lipstick, lip cream, eye liner, tooth paste, deodorant, cologne, hair restorer, hair nourishing composition and the like. Moreover, the emulsifier of the present invention can also be used for the production of ointment or fomentation. These emulsified compositions can be produced by using only the emulsifier of the present invention as the emulsifier.

The method for producing an emulsified composition by using the emulsifier of the present invention as an emulsifier is not particularly limited. Therefore, an emulsified composition can be produced by a method well known to those skilled in the art. Although most emulsified compositions can sufficiently be produced by using only the emulsifier of the present invention as an emulsifier, it is also possible to use it together with a known emulsifier.

As the method for producing an emulsified composition using the emulsifier of the present invention, for example, the production method using the D-phase emulsification can be exemplified. The D-phase emulsification is explained in detail in FRAGRANCE JOURNAL 1993–4, p.34.

As a specific production method, for example, an emulsified composition can be produced by mixing the emulsifier of the present invention with a polyhydric alcohol and a fat or oil component to form a gel, and emulsifying the gel through mixing with an aqueous component. By this method, fine emulsions can be formed. In this production method, the polyhydric alcohol and the fat or oil component are gelled by mixing with the emulsifier of the present invention. In this case, unless the fat or oil component is slowly added to the emulsifier of the present invention dissolved in the polyhydric alcohol, good gelation cannot generally be obtained. For this reason, it is desirable to gradually add the fat or oil component while operating a homogenizer such as Disper and homomixer. Further, in this production method, when a plurality of fat or oil compositions different in their kind and concentration are used, they are preferably added separately and sequentially, not added simultaneously. When the fat or oil components are added successively, the viscosity of the mixture is gradually decreased. Therefore, it is preferred that the stirring speed of the homogenizer is gradually lowered.

The fat or oil component prepared as described above is mixed with the aqueous component. While the method for this mixing is not particularly limited, it is preferable to uniformly mix them by using a homogenizer or the like. After the mixing, and optionally degassing and the like, a desired emulsified composition can be obtained.

The composition of the emulsified composition produced by using the emulsifier of the present invention is not particularly limited. A preferred emulsified composition is an oil in polyhydric alcohol type emulsified composition containing the emulsifier of the present invention, the polyhydric alcohol and the oil component as essential components. A particularly preferred emulsified composition contains 0.05 to 30% by weight of the emulsifier of the present invention as the sole emulsifier, 1 to 60% by weight of the polyhydric alcohol, and 10 to 90% by weight of the oil component.

The emulsified composition produced by using the emulsifier of the present invention may contain various components other than the sphingoglycolipid depending on its purpose. For example, it may contain ingredients suitable for the improvement of emollient effect, improvement of feeling upon use, alleviation of crust after use, improvement of solubility, alleviation of stretched feeling after use, improvement of adhesion to the skin, improvement of spread on the skin, alleviation of stickiness, prevention of skin roughening, improvement of skin care effect, improvement of skin protection effect, improvement of keratin, normalization of epithelial cornification (prevention of deficient cornification due to acceleration of skin turn over, prevention of pachymenia and suppression of epithelial lipid metabolic error), alleviation of xeroderma such as senile xeroderma, improvement of dry skin conditions such as crazing and desquamation, suppression of wrinkle generation, elimination of wrinkles, wound treatment, prevention and improvement of pigmentation, prevention of senescence, alleviation of dandruff and itching, alleviation of unhairing, prevention and treatment of scalp diseases, improvement of preservative quality, improvement of plasticity, improvement of elasticity, gloss impartation, inhibition of melanin production, prevention of suntan and the like.

Depending on the purpose of use, the emulsified composition of the present invention may further contain, for example, a fat and oil component, UV absorber, IR absorber, antiseptic, fungicide, antioxidant, whitening agent, vitamin, amino acid, hormone, peptide, physiologically active plant extract, fluorescent substance, pigment, coloringmatter, aromatic, scrub agent, sequestering agent, binder, extender, thickener, saccharide, nutrition ingredient, pH regulator, chelating agent, germicide, keratin improvement agent, keratin resolvent, antibiotic, skin permeation accelerator, blood circulation accelerator, resolution agent, cell activator, anti-inflammatory agent, analgesic, skin softener, skin emollient, wound treatment agent, metabolism accelerator and the like. Further, moisturizing agents other than the sphingoglycolipid represented by the formula (I) can also be added.

As the fat and oil component which can be used for the emulsified composition of the present invention, there can be mentioned, for example, fatty acids (e.g., oleic acid, behenic acid, isostearic acid, lauric acid, myristic acid, palmitic acid, stearic acid, linolic acid, γ-linolenic acid, columbinic acid, eicosa- (n-6, 9, 13)-trienoic acid, arachidonic acid, α-linolenic acid, timnodonic acid, hexaenoic acid etc.), ester oils (e.g., pentaerythritol-tetra-2-ethyl hexanoate, isopropyl myristate, butyl stearate, hexyl laurate, octyldodecyl myristate, diisopropyl adipate, diisopropyl sebacate, isopropyl myristate, octyldodecyl myristate, neopentyl glycol dioctanoate, neopentyl glycol dicaprate, diisostearyl malate, di(2-heptylundecyl)adipate, octyldodecyl lactate, isotridecyl isonanonate, cetyl isooctanoate, vitamin A palmitate etc.), waxes (e.g., bee wax, spermaceti wax, lanolin, carnauba wax, candelilla wax, vaseline etc.), animal oils and vegetable oils (e.g., mink oil, olive oil, castor oil, cacao butter, palm oil, cod liver oil, beef tallow, butter fat, evening primrose oil, rice bran oil, squalane, sesame oil, safflower oil, macadamia nut oil, jojoba oil, lanolin, mink oil, turtle oil etc.), mineral oils (e.g., hydrocarbon oil, liquidparaffin etc.), hydrocarbons(α-olefinoligomers, liquid isoparaffin etc.), silicone oils (e.g., dimethylpolysiloxane, methylphenylpolysiloxane, octamethylcyclotetrasiloxane, decamethylcyclopentanesiloxane etc.), higher alcohols (e.g., lauryl alcohol, stearyl alcohol, isostearyl alcohol, oleyl alcohol, cetyl alcohol, 2-hexyldecanol, 2-octyldodecanol, 2-decyltetradecanol, cholesterol, phytosterol etc.), triglycerides (e.g., glyceryl trioctanoate, tri(capryl and capric acid) glycerin), and derivatives thereof. Further, as organic acids, α-hydroxy acids, hydroxycarboxylic acids, dicarboxylic acids, glycyrrhizinic acid, glycyrrhetinic acid, mevalonic acid(mevalonolactone) and the like can be used.

Examples of the UV absorber which can be used for the emulsified composition of the present invention include, for example, oxybenzone(2-hydroxy-4-methoxybenzophenone), oxybenzonesulfonic acid, oxybenzonesulfonic acid trihydrate, guaiazulene, ethylene glycol salicylate, octyl salicylate, dipropylene glycol salicylate, phenyl salicylate, homomenthyl salicylate, methyl salicylate, methyl diisopropylcinnamate, cinoxate(2-ethoxyethyl p-methoxycinnamate), glyceryl di-p-methoxycinnamate mono-2-ethylhexanoate, dihydrozymethoxybenzophenone, sodium dihydroxymethoxybenzophenone-disulfonate, dihydroxybenzophenone, tetrahydroxybenzophenone, p-aminobenzoic acid, ethyl p-aminobenzoate, glyceryl p-aminobenzoate, amyl p-dimethylaminobenzoate, 2-ethylhexyl p-dimethylaminobenzoate, p-hydroxyanisole, 2-ethylhexyl p-methoxycinnamate, isopropyl p-methoxycinnamate, cinnamic acid diisopropyl ester, 2-(2-hydroxy-5-methylphenyl)benzo-triazole, sodium hydroxymethoxybenzophenonesulfonate, 4-tert-butyl-4'-methoxybenzoylmethane, 2-ethylhexyl salicylate, glyceryl p-aminobenzoate, methyl o-aminobenzoate, 2-hydroxy-4-methoxybenzophenone, amyl p-dimethylaminobenzoate, 2-phenylbenzimidazole-5-sulfonic acid, 2-hydroxy-4-methoxy-benzophenone-5-sulfonic acid, digalloyl trioleate, 2-ethoxyethyl p-methoxysilicate, butylmethoxybenzoylmethane, glyceryl-mono-2-ethylhexanoyl-di-p-methoxybenzophenone, 2-ethylhexyl-2-cyano-3,3'-diphenyl acrylate, 2,2'-dihydroxy-4-methoxybenzophenone, ethyl 4-bishydroxypropylaminobenzoate and the like.

Examples of the powdered material which can be used for the emulsified composition of the present invention include, for example, talc, Kaolin, fuller's earth, rubber, starch, silica, silicic acid, aluminum silicate hydrate, chemically modified magnesium aluminum silicate, poly(sodium acrylate), tetraalkylarylammonium snuctite, trialkylarylammonium snuctite, ethylene glycol monostearate, sodium carboxymethylcellulose, carboxyvinyl polymer, chalk, gummy substance, ethylene glycol monostearate, ethylene glycol distearate and the like.

As the polyhydric alcohol which can be used for the emulsified composition of the present invention, glycerin, polyglycerin such as diglycerin, triglycerin, tetraglycerin, and pentaglycerin, ethylene glycol, diethylene glycol, triethylene glycol, propylene glycol, 1,3-butylene glycol, 1,4-butylene glycol, 1,2-pentanediol, dipropylene glycol, polyethylene glycol, sorbitol, erythritol, pentaerythritol, maltotriose, threitol, sucrose, glucose, maltose, maltitose, fructose, xylitose, inositol and the like can be exemplified.

Examples of other ingredients which can be used for the emulsified composition of the present invention include, for example vitamins (e.g., vitamin A, vitamin $B_1$, vitamin $B_2$, vitamin $B_6$, vitamin $B_{12}$, vitamin C, vitamin D, vitamin E, vitamin K etc.), amino acids (e.g., proline, leucine, isoleucine, alanine, threonine, lysine, cysteine, arginine etc.), hormones (e.g., follicle hormone, pregnenolone, adrenocortical hormone etc.), peptides (e.g., keratin, collagen, elastin etc.), saccharides (e.g., those exemplified for polyhydric alcohol etc.), mineral salts (e.g., sodium chloride, sodium hydrogencarbonate, sodium carbonate, borax, sodium sulfate, sodium sulfide, sodium thiosulfate, sodium sesquicarbonate, magnesium oxide, calcium carbonate, magnesium carbonate, potassium chloride, potassium sulfide etc.), lactic acid bacteria culture product, sterols (e.g., cholesterol, provitamin $D_3$, campesterol, stigmastanol, stigmasterol, 5-dihydrocholesterol, α-spinasterol, fatty acid cholesterol ester etc.), sphingosines (e.g., sphingosine, dihydrosphingosine, phytosphingosine, dehydrosphingosine, dehydrophytosphingosine, sphingadienine etc.), ceramides, pseudoceramides, saponin, chitin derivatives, oligosaccharides (e.g., maltose, xylobiose, isomantose, lactose, sucrose, raffinose, maltotriose, xylotriose, maltotetraose, xylotetraose, maltopentaose, xylopentaose, maltohexaose, xylohexaose, maltoheptaose, xyloheptaose etc.), acidic mucopolysaccharides (e.g., hyaluronicacid, chondroitinsulfate, dermatan sulfate, heparin, heparan sulfate etc.), yeast extract and the like.

The emulsified composition of the present invention may further contain a thickener (e.g., carboxyvinyl polymer, carboxymethylcellulose, polyvinyl alcohol, carrageenan, alginate, alginic acid propylene glycol ester, gelatin, electrolytes such as sodium chloride etc.), skin whitening agent (e.g., arbutin, allantoin, vitamin E derivative, glycyrrhizin, magnesium salt of ascorbic acid and phosphoric acid ester, kojic acid, pantothenic acid derivative, placental extract, coix seed, green tea, pueraria root, mulberry bark, Glycyrrhiza, scutellariae radix, aloe, bitter orange peel, camomile, Litchi chinensis etc.), skin protective agents (e.g., retinol, retinol ester, retinoicacidetc.), skinsofteners (e.g., stearylalcohol, glyceryl monoricinoleate, mink oil, cetyl alcohol, stearic acid, palm oil, castor oil, orth-stearic acid etc.), skin emollients (e.g., stearyl alcohol, monorecinoleic acid glyceride, monostearic acid glyceride, cetyl alcohol etc.), skin permeation accelerator (e.g., 2-methylpropan-2-ol, 2-propanol, ethyl-2-hydroxypropanoate, 2,5-hexanediol, acetone, tetrahydrofuran etc.), physiologically active plant extracts (e.g., extracts of aloe, Arnica montana, Glycyrrhiza glabra, sage, Swertia japonica etc.), preservatives (e.g., p-hydroxybenzoic acid ester, sodium benzoate, urea, methylparaben, ethylparaben, propylparaben, butylparaben etc.), anti-inflammatory agents (e.g., salicylicacidetc.), germicides (e.g., triclosan etc.), antioxidants (e.g., α-tocopherol, butylhydroxytoluene etc.), buffers (e.g., combinations of triethanolamine or sodium hydroxide and lactic acid etc.), keratinresolvents (e.g., lactic acid, glycolicacid, malic acid, tartaric acid, citric acid etc.), scrub agents (e.g., polyethylene powder etc.), pigments (e.g., lakes of calcium, barium, and aluminium, iron oxide, titanium dioxide, mica etc.) and the like.

Ingredients other than those mentioned above can also be added to the emulsified composition of the present invention depending on its purpose. Addition amount and addition method for each ingredient may be selected according to amounts and techniques known in the art.

The emulsified composition of the present invention can be widely used for cases where moisturizing effect and anti-atopy effect are required. The amount to be used is decided within a range that sufficiently affords desired moisturizing effect.

Hereinafter, the present invention will be explained more specifically with reference to the following examples. The ingredients, ratios, operational sequences and the like shown in the following examples may be suitably changed unless it departs from the concept of the present invention. Therefore, the scope of the present invention is not limited by the examples shown below.

In the following Examples 1 to 4, each ingredient indicated in Table 1 was used as an emulsification active ingredient of the sphingoglycolipid represented by the formula (I). All of the sphingoglycolipids contained as the active ingredient had a normal chain alkyl group having a carbon number of 12 as $R_3$.

TABLE 1

| Active ingredient | $R_1$ | $R_2$ | Weight part |
|---|---|---|---|
| 1 | Structure A | Structure a | 1.00 |
| 2 | Structure A | Structure b | 1.00 |
| 3 | Structure A | Structure c | 1.00 |
| 4 | Structure B | Structure a | 1.00 |
| 5 | Structure B | Structure b | 1.00 |
| 6 | Structure B | Structure c | 1.00 |
| 7 | Structure C | Structure a | 1.00 |
| 8 | Structure C | Structure b | 1.00 |
| 9 | Structure C | Structure c | 1.00 |
| 10 | Structure D | Structure a | 1.00 |
| 11 | Structure D | Structure b | 1.00 |
| 12 | Structure D | Structure c | 1.00 |
| 13 | Structure A | Structure a | 0.50 |
|  | Structure A | Structure b | 0.50 |
| 14 | Structure B | Structure a | 0.50 |
|  | Structure B | Structure b | 0.50 |
| 15 | Structure A | Structure a | 0.50 |
|  | Structure B | Structure a | 0.50 |
| 16 | Structure A | Structure b | 0.50 |
|  | Structure B | Structure b | 0.50 |
| 17 | Structure A | Structure a | 0.25 |
|  | Structure B | Structure a | 0.25 |
|  | Structure C | Structure a | 0.25 |
|  | Structure D | Structure a | 0.25 |
| 18 | Structure A | Structure b | 0.25 |
|  | Structure B | Structure b | 0.25 |
|  | Structure C | Structure b | 0.25 |
|  | Structure D | Structure b | 0.25 |
| 19 | Structure A | Structure a | 0.45 |
|  | Structure A | Structure b | 0.45 |
|  | Structure A | Structure c | 0.10 |
| 20 | Structure B | Structure a | 0.45 |
|  | Structure B | Structure b | 0.45 |
|  | Structure B | Structure c | 0.10 |
| 21 | Structure C | Structure a | 0.20 |
|  | Structure C | Structure b | 0.40 |
|  | Structure C | Structure c | 0.40 |
| 22 | Structure D | Structure a | 0.20 |
|  | Structure D | Structure b | 0.40 |
|  | Structure D | Structure c | 0.40 |

EXAMPLE 1

Preparation of Cosmetic Cream

The materials of Ingredients A shown in Table 2 were stirred with heating to form a uniform solution at 80° C. To this solution, Ingredient B was slowly added, while operating a homogenizer, to form a gel, which was further stirred for 30 minutes. Then, a mixed solution of Ingredient C was slowly added to the mixture, and it was stirred for 10 minutes. Further, a mixed solution of Ingredient D was slowly added to the mixture, and it was stirred for 10 minutes. Since the viscosity of the mixture was decreased as Ingredients C and D were added, the stirring speed of the homogenizer was gradually lowered.

Separately, the materials of Ingredient E were mixed at room temperature to prepare a uniform solution. To this solution, Ingredient F was added to form a uniform mixture, and Ingredient G was further added to it to prepare a uniform mixture.

The mixture of Ingredients A, B, C, and D was added to the mixture of Ingredients E, F, and G, and the whole mixture was homogenized and degassed to produce a cosmetic cream.

TABLE 2

| Ingredient | Weight part |
| --- | --- |
| (Ingredient A) | |
| Each active ingredient shown in Table 1 | 1.25 |
| Glycerin | 12.50 |
| Methyl p-hydroxybenzoate | 0.10 |
| (Ingredient B) | |
| Phytosqualane | 30.00 |
| (Ingredient C) | |
| Dipotassium glycyrrhizinate | 0.05 |
| Purified water | 2.50 |
| (Ingredient D) | |
| 1,3-Butylene glycol | 2.50 |
| Purified water | 1.10 |
| (Ingredient E) | |
| 1,3-butylene glycol | 4.00 |
| Methyl p-hydroxybenzoate | 0.15 |
| Purified water | 29.35 |
| (Ingredient F) | |
| Carboxyvinyl polymer solution (2% aqueous solution of Hibis Waco 103) | 15.00 |
| (Ingredient G) | |
| 10% Aqueous solution of potassium hydroxide | 1.50 |

EXAMPLE 2

Preparation of Emollient Cream

Emollient creams were produced in the same manner as in Example 1 using the ingredients indicated in the table mentioned below.

TABLE 3

| Ingredient | Weight part |
| --- | --- |
| Each active ingredient of Table 1 | 5.0 |
| Stearyl alcohol | 6.0 |
| Stearic acid | 2.0 |
| Hydrogenated lanolin | 4.0 |
| Squalane | 9.0 |
| Octyl dodecanol | 10.0 |
| 1,3-Butylene glycol | 10.0 |
| Coloring matter | 0.5 |
| Antiseptic | 0.1 |
| Antioxidant | 0.1 |
| Purified water | 53.3 |

EXAMPLE 3

Preparation of Hand Cream

Hand creams were produced in the same manner as in Example 1 using the ingredients indicated in the table mentioned below.

TABLE 4

| Ingredient | Weight part |
| --- | --- |
| Each active ingredient of Table 1 | 3.0 |
| Glycerin | 20.0 |
| Urea | 2.0 |
| Vaseline | 6.0 |
| Liquid paraffin | 10.0 |
| Purified water | 59.0 |

EXAMPLE 4

Preparation of Anti-atopy Ointment

Anti-atopy ointments were produced in the same manner as in Example 1 using the ingredients indicated in the table mentioned below.

TABLE 5

| Ingredient | Weight part |
| --- | --- |
| Each active ingredient of Table 1 | 3.0 |
| Vaseline | 24.0 |
| Stearyl alcohol | 21.0 |
| Propylene glycol | 13.0 |
| Antiseptic | 0.2 |
| Purified water | 38.8 |

The sphingoglycolipids disclosed in the present specification have marked moisturizing effect, skin roughening preventing effect, and emulsifying effect. Therefore, the emulsifiers of the present invention containing these sphingoglycolipids are very useful for the production of emulsified compositions including moisturizers, skin roughening inhibitors and the like. For this reason, the emulsifiers of the present invention can be widely used for the various products including cosmetic and medical products that are directly applied to the skin.

What is claimed is:

1. A method for producing an emulsified composition comprising mixing an emulsifier with polyhydric alcohol and a fat or oil component to form a gel, and emulsifying the gel through mixing with an aqueous component, wherein said emulsifier contains a sphingoglycolipid which has a structure represented by the following formula:

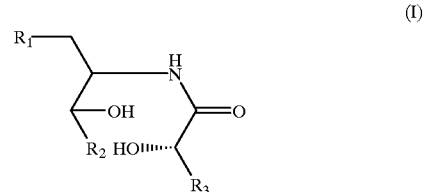

(I)

wherein $R_1$ is a saccharide moiety which consists of (i) three to four hexoses selected from the group consisting of uronic acid, glucosamine, galactose, and mannose, or (ii) one uronic acid, $R_2$ is an alkyl group which may have a cycloalkyl group, a hydroxyl substituted alkyl group, an alkenyl group, or an alkynyl group, and $R_3$ is an alkyl group or a hydroxyl substituted alkyl group.

2. The method of claim 1 wherein $R_1$ in the emulsifier consists of three or four hexoses.

3. The method of claim 2 wherein $R_1$ in the emulsifier is (i) a saccharide moiety consisting of four hexoses of uronic acid, glucosamine, galactose, and mannose, (ii) a saccharide moiety consisting of three hexoses of uronic acid, glucosamine, and galactose, or (iii) a saccharide moiety consisting of four hexoses of uronic acid, galactose, and two glucoses.

4. The method of claim 1 wherein $R_1$ of the emulsifier has a structure represented by any one of the following formulas:

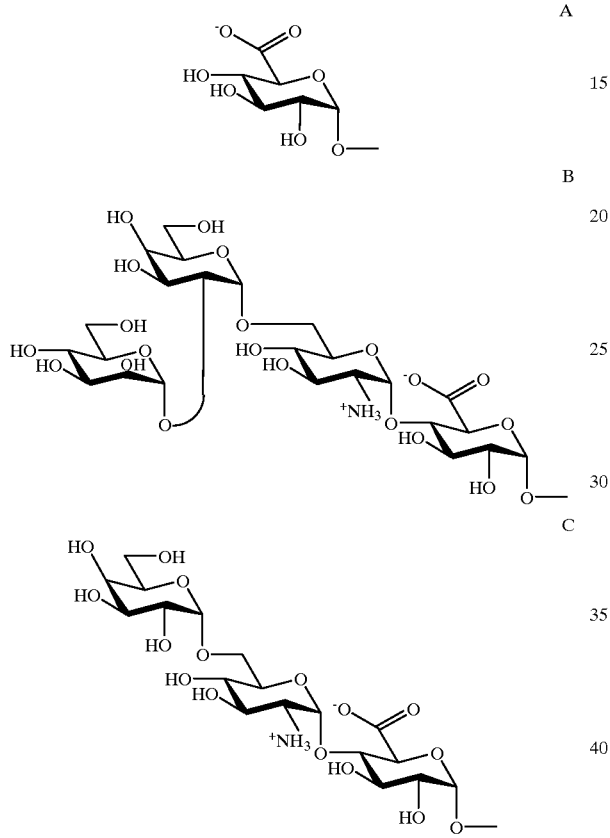

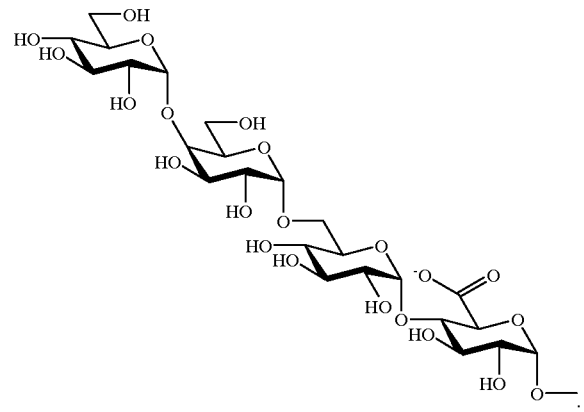

5. The method of claim 4 wherein $R_3$ in said emulsifier is a normal chain alkyl group having a carbon number of 12.

6. The method of claim 1 wherein $R_2$ in the emulsifier has a carbon number of 15–25.

7. The method of claim 6 wherein $R_2$ in the emulsifier has a structure represented by any one of the following formulas:

a: $CH_3(CH_2)_{14}$—— b: $CH_3(CH_2)_5$——$\underset{\underset{CH_2}{\diagdown\diagup}}{CH-CH}$——$(CH_2)_9$—— c: $CH_3(CH_2)_5 CH\!=\!\!=\!\!CH(CH_2)_9$——.
(cis)

8. The method of claim 7 wherein $R_3$ in said emulsifier is a normal chain alkyl group having a carbon number of 12.

9. The method of claim 1 wherein $R_3$ in the emulsifier is a substituted or unsubstituted normal chain alkyl group having a carbon number of 10–20.

10. The method of claim 9 wherein $R_3$ in the emulsifier is a normal chain alkyl group having a carbon number of 12.

* * * * *